United States Patent
van't Hooft

[11] Patent Number: 5,720,301
[45] Date of Patent: Feb. 24, 1998

[54] GUIDE TUBE HAVING AT LEAST ONE CHANNEL FOR GUIDING A CABLE

[76] Inventor: Eric van't Hooft, Gezichtslaan 16, 3956 BB Leersum, Netherlands

[21] Appl. No.: 748,913

[22] Filed: Nov. 13, 1996

Related U.S. Application Data

[63] Continuation of Ser. No. 417,144, Apr. 4, 1995, abandoned, which is a continuation of Ser. No. 81,450, Jun. 25, 1993, abandoned.

[30] Foreign Application Priority Data

Jun. 25, 1992 [NL] Netherlands ............... 9201132

[51] Int. Cl.⁶ ..................................... A61B 5/00
[52] U.S. Cl. ..................................... 128/772; 604/94
[58] Field of Search ............... 128/772; 606/191, 606/192, 194, 198; 600/3, 30; 604/94, 95, 171

[56] References Cited

U.S. PATENT DOCUMENTS

| | | | |
|---|---|---|---|
| 4,553,271 | 11/1985 | Baker | 600/30 X |
| 4,898,577 | 2/1990 | Badger et al. | 606/194 X |
| 5,201,756 | 4/1993 | Horzewski et al. | 606/198 |
| 5,255,668 | 10/1993 | Umeda | 128/772 X |

FOREIGN PATENT DOCUMENTS

| | | |
|---|---|---|
| 0254351 | 1/1988 | European Pat. Off. |
| 2645354 | 10/1990 | France. |
| 3714492 | 11/1987 | Germany. |

*Primary Examiner*—Sam Rimell
*Attorney, Agent, or Firm*—Griffin, Butler, Whisenhunt & Kurtossy

[57] ABSTRACT

A guide tube having at least one channel for guiding a cable has an elongated cylindrical sheath body incorporating at least two pull wires, located in the same diametrical plane of the guide tube. The sheath body may be composed of several parts, and a number of channels may be formed with a sheath body, which channels may or may not be separable from each other.

6 Claims, 2 Drawing Sheets

GUIDE TUBE HAVING AT LEAST ONE CHANNEL FOR GUIDING A CABLE

This application is a continuation of Ser. No. 08/417,144, filed Apr. 4, 1995, now abandoned, which in turn is a continuation of Ser. No. 08/081,450 filed Jun. 25, 1993, now abandoned.

The invention relates to a guide tube having at least one channel for guiding a cable, in particular a cable comprising at one end thereof an element for the local treatment of a part of the body of a patient, which element can be transported through the guide tube by means of the cable, the guide tube comprising an elongated cylindrical body in which a pull wire is incorporated.

Such a guide tube, disclosed in EP-A-0 254 351, is composed of a helical spring having adjoining windings and surrounded by a synthetic plastics sheath. Such a guide tube is used for transporting, by means of the cable, a control element or a radiation source from a safe to a precisely predetermined location in a part of the body of a patient. To prevent the length of the guide tube from changing, as a result of for instance a tensile force, such that the radiation source, mounted on the leading end of the cable, no longer ends up precisely at the desired predetermined location, a pull wire is arranged along the outer side of the helical spring and inside the synthetic plastics sheath, which pull wire is attached by one end thereof to a connector at one end of the guide tube. In this manner, the guide tube is protected against its being pulled apart in the longitudinal direction. If the guide tube is laid in a number of bends or loops, the pull wire will have the tendency to lie in the inside bend. Because the pull wire is located at a distance, albeit a short one, from the centre line of the guide tube, this means, in the case of a non-upsetting pull wire, that the length of the centre line will become somewhat longer owing to one-sided, arcuate expansion of the helical spring. Although this involves only a slight dimensional variation, this can be undesirable in the case where an exact positioning of the element mounted on the end of the guided cable is intended. Further, in view of its construction and component parts, the known guide tube is relatively expensive.

The object of the invention is to provide a guide tube of the type referred to in the opening paragraph hereof, which does not present the above-described problems.

According to the invention, this is realized in that at least two pull wires are incorporated in the sheath body, said pull wires being substantially located in the same diametrical plane of the guide tube. By these features, on the one hand, a protection against the guide tube being pulled apart is obtained, as was the case with the known guide tube, while, on the other hand, a protection is also obtained against the relative extension of the centre line of the channel when the guide tube is laid in bends or loops. The diametrically opposite pull wires define a preferred bending plane, comprising, in addition to the two pull wires, the centre line of the channel of the guide tube, so that when the guide tube is bent, the length of the centre line of the channel, located in the bending plane, remains unchanged and equal to that of the pull wires. Thus, a guide tube is obtained which preferably bends in one direction only and which is particularly stiff in flexure in a plane perpendicular thereto.

Further, such a guide tube is relatively simple and inexpensive to manufacture, for instance by means of extrusion molding. If a guide tube is started from a sheath body, like that of the known guide tube and, is composed of at least two concentric cylindrical parts, then, according to a preferred embodiment of the invention, there are provided an inner cylindrical part made of a hard, wear-resistant material with a low friction, and an outer cylindrical part made of a tough material with a high resistance to kinking. In this manner, a combination of properties can be obtained which renders the functioning of the guide tube as a protection element and transport guide for the cable with treatment element as reliable as possible.

In order to obtain an optimum connection between the pull wires and the synthetic material covering these wires, it is preferred that, in accordance with a further embodiment of the invention, the pull wires be embedded in the inner cylindrical part. At the same time, the pull wires will then be positioned as closely as possible to the cable to be guided and protected, which further reduces the chances of deviations owing to elongation.

In the case of local treatments, it may be preferred that a particular area be approached from different sides. In such a case, several guide tubes with cables can be used. According to a further embodiment of the invention, it may then be preferred that the inner cylindrical part comprise at least two channels, at least coupled to each other by the outer cylindrical part.

In the case of several channels one may choose to have one pull wire extending between two adjacent channels. This embodiment is preferred if the guide tube with several channels should extend, for instance, from a first fixed coupling point to a second fixed coupling point. If at one end the guide tube with several channels should extend to a number of separate connecting points for the channels, it is preferred that two adjacent inner cylindrical parts can be separated from each other, at least partially, by pulling apart or cutting loose at least the outer cylindrical part.

The guide tube according to the invention will be further described and illustrated hereinafter with reference to the exemplary embodiments shown in the drawings.

Figure 1:
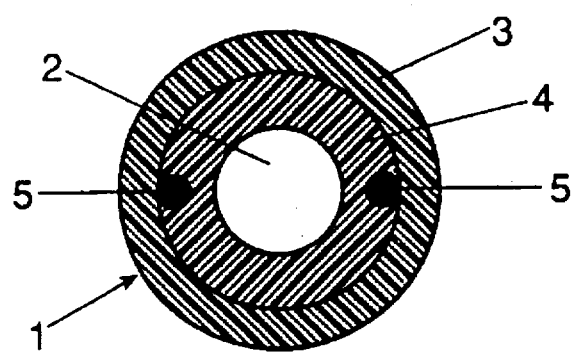
FIG. 1 shows in cross section a first embodiment of the guide tube according to the invention.
Figure 2:
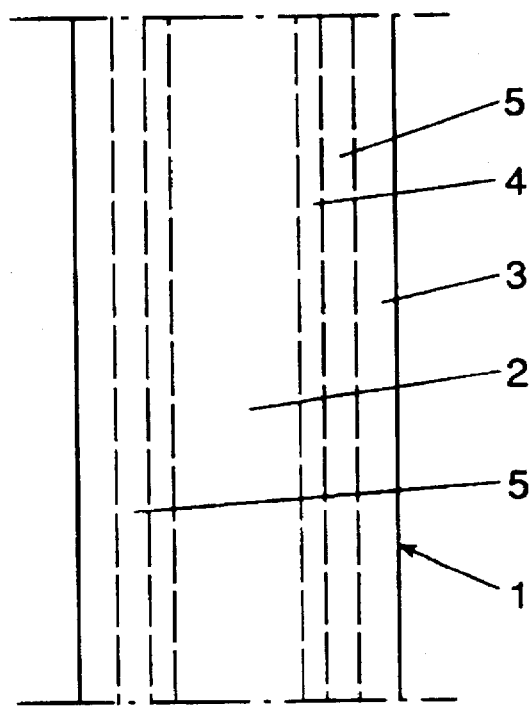
FIG. 2 shows in top plan view the guide tube of FIG. 1.

FIGS. 1 and 2 show a guide tube 1 with a central channel 2, which guide tube 1 is composed of an outer cylindrical part 3, an inner cylindrical part 4 and two diametrically opposite pull wires 5, embedded in the inner cylindrical part 4.

The inner cylindrical part 4 surrounds the channel 2 and, for the purpose of an optimum guidance of the cable (not shown), is preferably made of a wear-resistant material having a low coefficient of friction. In practice, this usually means the material is a hard and rigid synthetic material, which, accordingly, is sensitive to kinking. Because a kink in the guide tube 1 would impede the contemplated treatment owing to a blocking of the channel 2, in order to reduce the sensitivity to kinking, the outer cylindrical part 3 is made of a tough synthetic material having a high resistance to kinking. The pull wires 5 are preferably made of a metal, for instance a steel wire or a similar wire, and if so desired, with the possibility of guiding signals. Such a guide tube can be manufactured in a relatively simple manner by means of extrusion molding, with the pull wires 5 being embedded in the synthetic material of the inner cylindrical part 4.

By embedding the pull wires 5 diametrically opposite each other, a guide tube 1 is produced which can be bent relatively easily in a first direction, i.e., as viewed in FIG. 2, upwards from the plane of the drawing, but which is relatively stiff in bending in a second direction perpendicular thereto, i.e., as viewed in FIG. 2, to the left and to the right. In this manner, as a result of the presence of the pull wires 5, a guide tube 1 is obtained which, at least within a given range, will hardly become any longer or shorter, if at all, during tensile or pressure forces, and the channel 2 of which, when the tube is laid in bends or loops, has a centre line whose length remains the same as a result of the pull wires 5 being diametrically opposite.

Figure 3:
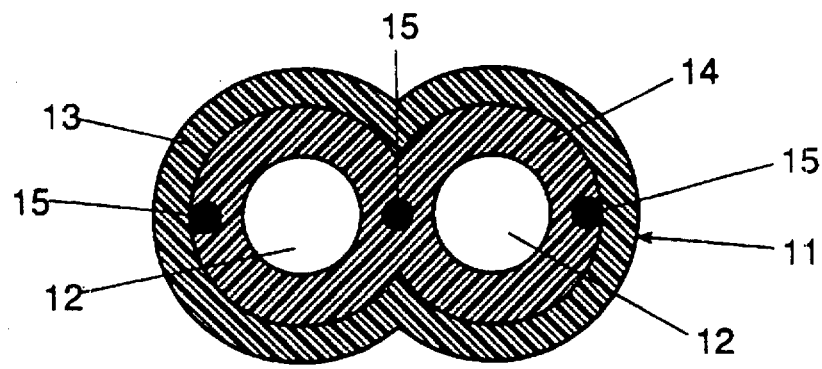
FIG. 3 shows in cross section a second embodiment of the guide tube according to the invention.

FIG. 3 shows in cross section a guide tube 11 with two channels 12, surrounded by an eight-shaped inner cylindrical part 14, which in turn is surrounded by an eight-shaped outer cylindrical part 13. According to the teachings of the invention, pull wires 15 are again present, which are all located in a diametrical plane of the channel 12, because two channels 12 are present in the common diametrical plane of the two channels 12. In this embodiment, too, each channel 12 comprises two diametrically opposite pull wires 15, with the understanding that the central pull wire 15 is a common or coinciding pull wire for both channels 12.

Figure 4:
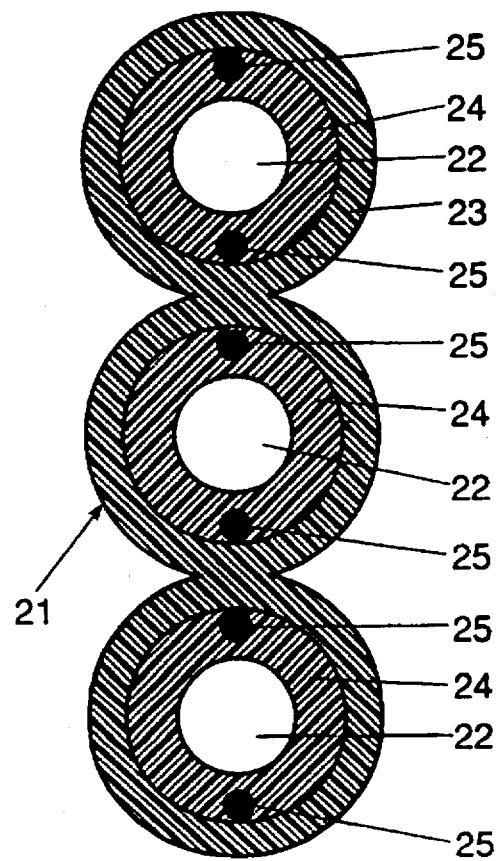
FIG. 4 shows in cross section a third embodiment of the guide tube according to the invention.

FIG. 4 shows in cross section a guide tube 21 having three channels 22, each channel being surrounded by a separate inner cylindrical part 24 incorporating two diametrically opposite pull wires 25, while the three inner cylindrical parts 24 are held together by a common outer cylindrical part 23. In this embodiment of the guide tube, the channels 22 can be handled as a one-piece guide tube through a common path. However, should the channels 22 follow different routes through a part of the path, this is possible by tearing loose or cutting the outer cylindrical part 23 through a certain distance, whereupon each channel 22, defined by an inner cylindrical part 24 with embedded pull wires 25, can be positioned in the desired manner.

It will be clear that within the framework of the invention many modifications and variants are possible. For instance, the guide tube can have any number of channels other than one, two or three. In addition, further cylindrical parts may be present between the outer and the inner cylindrical parts, for instance a layer which adheres well to the two other cylindrical parts if these latter parts do not properly adhere to each other, or a layer of woven metal wire providing an additional protection and strength. Although substantially circular cross-sections are shown, they may have any other cross-section as well. For instance, the outer circumference of the outer cylindrical part can very suitably have a polygonal shape.

I claim:

1. A guide tube for guiding a cable therethrough, comprising an elongated sheath body having at least one unitary innermost part with at least one longitudinally extending channel therein with a center line, and at least two longitudinally extending pull wires embedded within the at least one innermost part and each pull wire having a center line, wherein the center line of each channel lies between the center lines of the at least two pull wires and all the center lines of all channels and pull wires present lie in substantially one single plane such that when the tube is laid in bends or loops the center line length of each of the at least one channels remains unchanged.

2. A guide tube according to claim 1, wherein the at least one inner part containing the at least one channel is made of a hard, wear-resistant material having a low friction and an outer part made of a tough material having a high resistance to kinking surrounds the at least one inner part.

3. A guide tube according to claim 1, wherein there are at least two inner parts, each containing a channel, and the parts are coupled to each other at least by the outer part.

4. A guide tube according to claim 3, wherein one pull wire extends between two adjacent channels.

5. A guide tube according to claim 3, wherein adjacent inner parts are at least partially separable from each other by pulling apart or cutting loose at least the outer part.

6. A guide tube for guiding a cable therethrough, comprising an elongated sheath body having at least one cylindrical, unitary, solid innermost part with at least one longitudinally extending channel having a center line and forming an inside surface of the innermost part, and at least two longitudinally extending metal pull wires embedded within the at least one innermost part and each pull wire having a center line, wherein the center line of each channel lies between the center of the at least two pull wires and all the center lines of all channels and pull wires present lie in substantially one single plane such that when the tube is laid in bends or loops the center line length of each of the at least one channels remains unchanged.

* * * * *